(12) United States Patent
Misaki et al.

(10) Patent No.: US 8,153,163 B2
(45) Date of Patent: Apr. 10, 2012

(54) PEARLESCENT PIGMENT

(75) Inventors: Eiichiro Misaki, Sumida-ku (JP); Hiroyuki Shiomi, Haga-gun (JP); Maoya Adachi, Tachikawa (JP); Takahiro Kaida, Tachikawa (JP)

(73) Assignees: Kao Corporation, Tokyo (JP); Nihon Koken Kogyo KK, Tachikawa-shi (JP)

( * ) Notice: Subject to any disclaimer, the term of this patent is extended or adjusted under 35 U.S.C. 154(b) by 0 days.

(21) Appl. No.: 13/170,898

(22) Filed: Jun. 28, 2011

(65) Prior Publication Data

US 2011/0256194 A1    Oct. 20, 2011

Related U.S. Application Data

(63) Continuation of application No. 11/300,369, filed on Dec. 15, 2005, now Pat. No. 8,016,934.

(30) Foreign Application Priority Data

Dec. 16, 2004  (JP) ................. 2004-363966
Dec. 16, 2004  (JP) ................. 2004-363967

(51) Int. Cl.
*A01N 59/16*   (2006.01)
*A61K 33/26*   (2006.01)
*C09C 1/00*    (2006.01)
*C04B 14/20*   (2006.01)

(52) U.S. Cl. ........ 424/646; 424/647; 106/415; 106/417; 106/418; 106/439; 428/403

(58) Field of Classification Search ............... 424/70.1, 424/646–647; 106/415–418, 439; 428/403; 427/215, 218
See application file for complete search history.

(56) References Cited

U.S. PATENT DOCUMENTS

| | | | |
|---|---|---|---|
| 3,926,659 A | 12/1975 | Bernhard et al. | |
| 3,947,571 A | 3/1976 | Murphy et al. | |
| 4,425,329 A | 1/1984 | Tsutsumi et al. | |
| 4,867,793 A | 9/1989 | Franz et al. | |
| 5,273,576 A | 12/1993 | Sullivan et al. | |
| 5,423,912 A | 6/1995 | Sullivan et al. | |
| 5,522,923 A | 6/1996 | Kimura et al. | |
| 5,702,518 A | 12/1997 | Vogt et al. | |
| 5,972,098 A | 10/1999 | Andes et al. | |
| 6,001,373 A | 12/1999 | Igo-Kemenes et al. | |
| 6,596,070 B1 | 7/2003 | Schmidt et al. | |
| 6,602,340 B1 | 8/2003 | Schank et al. | |
| 7,173,052 B2 | 2/2007 | Bradley et al. | |
| 2002/0037262 A1 | 3/2002 | Tanaka et al. | |
| 2002/0192585 A1 | 12/2002 | Brenner et al. | |
| 2003/0044364 A1 | 3/2003 | Meyer et al. | |
| 2004/0166316 A1 | 8/2004 | Noguchi | |
| 2005/0014865 A1 | 1/2005 | Bagala et al. | |
| 2006/0144294 A1 | 7/2006 | Misaki et al. | |

FOREIGN PATENT DOCUMENTS

| | | |
|---|---|---|
| DE | 41 04 310 A1 | 8/1992 |
| EP | 0 589 681 A2 | 3/1994 |
| JP | 49-128027 | 12/1974 |
| JP | 54113445 | 9/1979 |
| JP | 03-197413 A | 8/1991 |
| JP | 04-128211 A | 4/1992 |
| JP | 6-100794 | 4/1994 |
| JP | 07-000759 | 1/1995 |
| JP | 7-11161 | 1/1995 |
| JP | 8-259840 | 10/1996 |
| JP | 09-12919 | 1/1997 |
| JP | 09-194754 | 7/1997 |
| JP | 2001-335433 | 12/2001 |
| JP | 2003-212722 | 7/2003 |
| WO | WO 2004-045524 A2 | 6/2004 |
| WO | WO 2004-061012 A2 | 7/2004 |
| WO | WO2004/104120 | 12/2004 |

OTHER PUBLICATIONS

Japanese Office Action issued on Feb. 8, 2011 for Japanese Patent Application No. 2005-363488 (w/Translation).

*Primary Examiner* — Jerry Lorengo
*Assistant Examiner* — Pegah Parvini
(74) *Attorney, Agent, or Firm* — Oblon, Spivak, McClelland, Maier & Neustadt, L.L.P.

(57) ABSTRACT

The present invention relates to a pearl pigment obtained by coating the surface of a flaky powder with a colored metal or a colored metal oxide and further coating the surface of the above colored metal- or colored metal oxide-coated flaky powder with a colorless metal or a colorless metal oxide, wherein when the pearl pigment is applied onto the surface of black artificial leather in an average amount of 0.05 mg/cm$^2$ and the intensity of light reflected from the pearl pigment is measured using illuminant C at a 2° viewing angle with a spectrophotometric colorimeter which is provided with a sheet polarizer S on the light incident side and a sheet polarizer P on the light receiving side, the powder reflection light which is incident to the pearl pigment as a measurement sample at an angle of 45° to the direction normal to the surface of the sample and is received in the direction normal to the surface of the sample has absolute values a* and b* of 10 or less, and make-up cosmetics containing the pearl pigment.

6 Claims, 1 Drawing Sheet

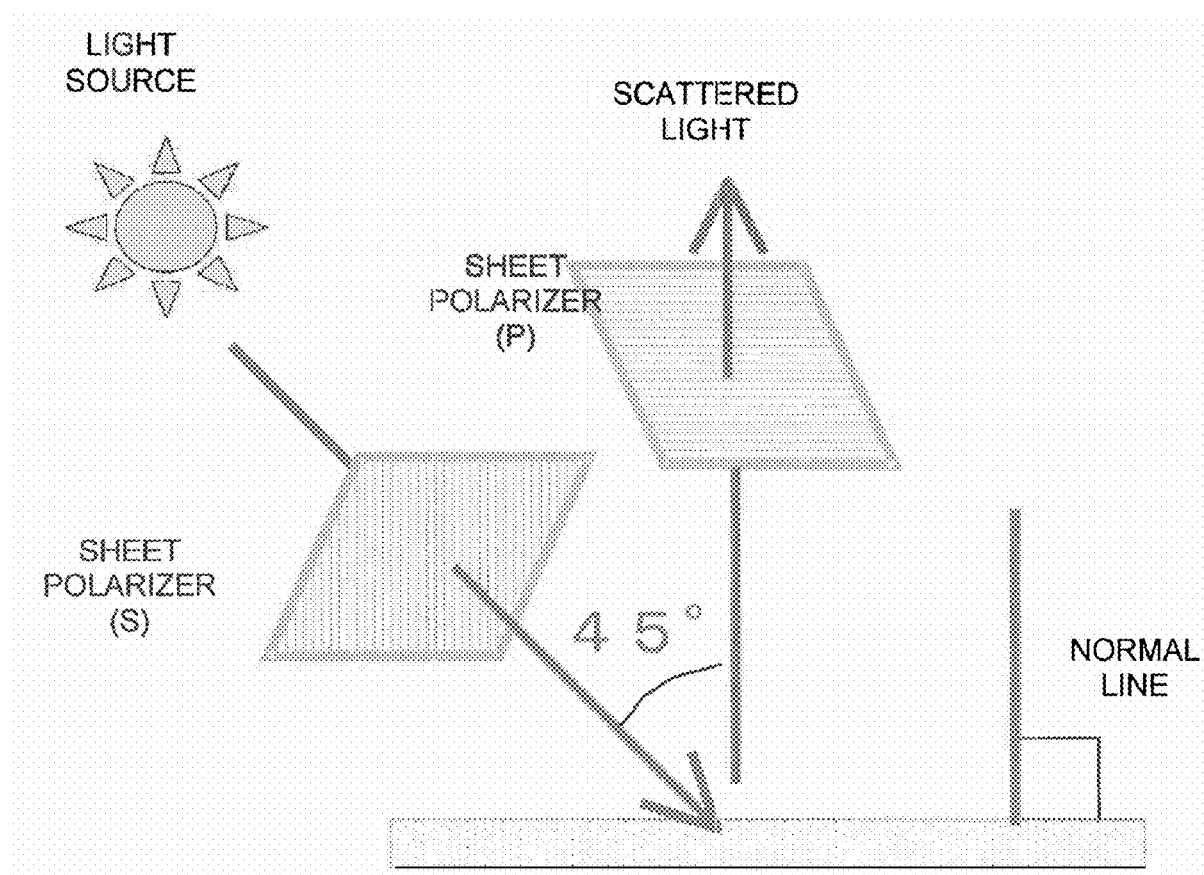

PEARLESCENT PIGMENT

This application is a Continuation of application Ser. No. 11/300,369, filed on Dec. 15, 2005, now U.S. Pat. No. 8,016,934.

FIELD OF THE INVENTION

The present invention relates to a pearl pigment, a process for producing the same, and make-up cosmetics containing the same.

BACKGROUND OF THE INVENTION

There have been used a variety of coloring pigments in areas such as coatings, plastics, printing inks and cosmetics. In recent years, there have been used light-interference pearl pigments which are obtained by coating the surface of flaky powder with titanium oxide, iron oxide or the like to obtain a bright color and a certain kind of design on products.

In commonly used pearl pigments, which are obtained by coating the surface of flaky powder with a colorless metal oxide such as titanium oxide, the thickness of the coating is varied, to produce a variety of interference colors. It is known that, for brighter interference colors, materials with different refractive indexes should be multi-layered. There have been proposed various methods for multi-layering such materials, and there are pearl pigments of multi-layer construction on the market, indeed. Meanwhile, in pearl pigments of multi-layer construction obtained using a color metallic compound such as iron oxide, it is also possible to obtain bright interference colors. Such pigments are, however, affected by the color of the color metallic compound, and there have been only pearl pigments having a color of similar shade to that of the color compound. For example, pearl pigments obtained using iron oxide each have a color of a reddish shade. In other words, no multi-layered pearl pigment in which the color of the color compound used as an inner layer is controlled and thus interference colors are produced without restrictions by the color of the color metallic compound itself has been known.

For example, in JP-A-6-100794 there are proposed multi-layer pearl pigments obtained by forming an iron oxide layer on a platelet-shaped powder and con inn the powder with the iron oxide layer with an aluminum compound. This proposal relates to pigments having a color of a reddish shade and a process for producing the same, and therefore provides only pearl pigments having a color of a reddish shade. In JP-A-7-11161 and JP-A-8-259840, there are proposed multi-layer pearl pigments obtained by coating iron oxide coated platelet-shaped powder with a colorless metal oxide such as titanium oxide. These proposals are, however, different from the above described proposal only in the kind of the colorless metal oxide used, and like the above proposal, they provide only pearl pigments having a color of a reddish shade. There is nothing described of obtaining pigments having a hue other than red in those specifications.

Meanwhile, of cosmetics using coloring pigments, make-up cosmetics are required to change users' skin texture when they apply them to their skin, and powders that give rise to strong diffuse reflection or specular reflection are used to control users' skin one and texture. For example, titanium oxide as a powder that gives rise to strong diffuse reflection or a spherical powder is blended with make-up cosmetics to create a matte finish, or a platelet-shaped powder, such as mica, sericite or talc, which gives rise to strong specular reflection is blended with make-up cosmetics to impart a lustrous finish. To cover color non-uniformity such as pigmented spots or freckles, pigments having good hiding power such as titanium dioxide or iron oxide are also blended with make-up cosmetics.

However, the use of pigments with good hiding power causes a problem of producing an unnatural look, whereas the use of powders with poor biding power to adjust the skin tone and texture causes a problem of a decrease in the covering effect on the color non-uniformity, etc., of the skin.

To overcome the above described problems, considerations have been given to using pearl pigments that have good hiding power and are capable of controlling skin luster to change the hue of the skin, in recent years. For example, when a titanium-oxide coated pearl pigment is used in cosmetics for imparting a lustrous finish to the skin, skin luster can be produced in such a direction that regular reflection of light occurs, due to the specular reflection by the pigment, but not through an angle other than that of specular reflection, and at such an angle the cosmetics impart a whitish look of the powder itself. Accordingly, when a user applies the cosmetics over a wide range, for example, to the entire face, portion directly facing its observer provides a lustrous look, but the portion not directly facing its observer provides a whitish and powdery look, resulting in a tendency toward an unnatural finish. JP-A-2003-212722 describes a powder for producing natural skin luster which is obtained by coating the surface of titanium mica with alumina and silica in this order. This powder, however, still leaves unresolved the problem of a whitish and powdery look produced on the portion that does not directly face its observer.

On the other hand, there are pearl pigments in which a coating is applied onto the colored metal oxide layer, such is iron oxide layer, on the market. In JP-A-7-11161 and 8-259840, there are proposed multi-layer pearl pigments obtained by coating an iron-oxide coated platelet-shaped powder with a colorless metal oxide such as titanium oxide. However, the pearl, pigments obtained are all reddish ones, and it is impossible to express a bright charming skin tone and texture by using them.

SUMMARY OF THE INVENTION

The present invention provides a pearl pigment having a flaky powder coated on the surface with a colored metal or a colored metal oxide, wherein the surface of the colored metal or colored metal oxide-coated flaky powder is coated with a colorless metal or a colorless metal oxide, wherein when the pearl pigment is applied onto the surface of black artificial leather in an average amount of 0.05 mg/cm$^2$ and the intensity of light reflected from the pearl pigment is measured using illuminant C at a 2° viewing angle with a spectrophotometric colorimeter which is provided with a sheet polarizer S on the light incident side and a sheet polarizer P on the light receiving side, the powder reflection light (scattered light) which is incident to the pearl pigment as a measurement sample at an angle of 45° to the direction normal to the surface of the sample and is received in the direction normal to the surface of the sample has absolute values a* and b* of 10 or less.

Further, the present invention provides a pearl pigment having a flaky powder with a colored metal or a colored metal oxide coated on the surface so that the average surface roughness is 10 nm or less and wherein the surface of the colored metal- or colored metal oxide-coated flaky powder is further coated with a colorless metal or a colorless metal oxide.

Further, the present invention provides a process for producing a pearl pigment which includes adding an aqueous solution of a colored metal oxide precursor to an aqueous dispersion of a flaky powder so that the amount of metal ion is $5\times10^{-4}$ to $12\times10^{-4}$ mol/min per 100 g of the flaky powder; adding an alkaline solution to the mixed solution so that the pH of the mixed solution is adjusted to 5 to 8; separating the solid from the mixed solution; baking the separated solid at 500 to 1000° C. to obtain a pearl pigment; suspending the obtained pearl pigment in water; adding an aqueous solution of a colorless metal or colorless metal oxide precursor to the suspension; adding an alkaline solution to the mixed solution so that the pH of the mixed solution is adjusted to 5 to 8; separating the solid from the mixed solution; and baking the separated solid at 500 to 1000° C.

Still further, the present invention provides a process for producing a pearl pigment which includes: adding an aqueous solution of a colored metal oxide precursor to an aqueous dispersion of a flaky powder so that the amount of metal ion is $5\times10^{-4}$ to $12\times10^{-4}$ mol/min per 100 g of the flaky powder; adding an alkaline solution to the above mixed solution so that the pH of the mixed solution is adjusted to 5 to 8; separating the obtained solid from the mixed solution; adding an aqueous solution of a colorless metal or colorless metal oxide precursor to a dispersion of the solid; separating the obtained solid from the mixed solution; and baking the separated solid at 500 to 1000° C.

Still further, the present invention provides make-up cosmetics that contain any one of the above described pearl pigments.

BRIEF DESCRIPTION OF THE DRAWINGS

FIG. 1 illustrates "the method for measuring the value a* and value b* of the present invention".

DETAILED DESCRIPTION OF THE INVENTION

The present invention relates to: a novel multi-layer pearl pigment which retards the production of scatter colors, takes advantage of the character of a colored metal compound and produces a variety of interference colors free from the color tone of the colored metal compound; a process for producing such a pearl pigment; and make-up cosmetics which contain the pearl pigment, thereby being capable of changing the hue of the skin while imparting a sheer dewy finish to the skin, creating a light smooth finish and producing a natural luster on the skin.

In the present invention, value a* and value b* each indicate chromaticity standardized by Commission International de L'Eclairage (CIE) (1976). The method for measuring the values a* and b* of each pearl pigment herein shown (see FIG. 1) is referred to as "the method for measuring the values a* and b* of the present invention".

The present inventors have found that a pearl pigment obtained by coating the surface of a flaky powder with a colored metal or a colored metal oxide and further coating the surface of the colored metal- or colored metal oxide-coated flaky powder with a colorless metal or a colorless metal oxide, wherein the absolute values of the values a* and b* of the scattered light measured under specified conditions are 10 or less, produces brilliant colors and that the use of such a pearl pigment makes it possible to obtain make-up cosmetics capable of changing the hue of the skin while imparting a sheer dewy finish to the skin, creating a light smooth finish and producing a natural luster on the skin, and they have finally accomplished the present invention.

The pearl pigment of the present invention produces brilliant colors while retarding the production of scatter colors. The make-up cosmetics of the present invention that contain the above described pearl pigment are capable of changing the hue of the skin while imparting a sheer dewy finish to the skin, creating a light smooth finish and producing a natural, luster on the skin. Their feeling in use, such as spreadability when applied to the skin, is also good.

The flaky powder used in the pearl pigment of the present invention is preferably 2 to 200 μm in average particle size and 0.01 to 5 μm in average thickness and, from the viewpoint of suitability for blending, more preferably 2 to 20 μm in average particle size and 0.05 to 1 μm in average thickness. The term "average particle size" used herein means volume average particle size (D4) (average particle size calculated based on volume fraction). The measurement can be made with ease and good reproducibility using a laser diffraction particle size distribution analyzer. For the thickness of the flaky particle, the difference from the reference surface is measured with an atomic force microscope and the arithmetic mean of the measurements is used as an average thickness.

Examples of flaky powders used in the pearl pigment of the present invention include: mica, sericite, talc, kaolin, smectite clay mineral, synthetic mica, synthetic sericite, platelet-shaped titanium dioxide, platelet-shaped silica, platelet-shaped aluminum oxide, boron nitride, barium sulfate, and platelet-shaped titania-silica composite oxide. Of these flaky powders, mica is preferable in terms of surface smoothness.

Examples of colored metals used for coating a flaky powder in the present invention include gold and copper. Of these metals, gold is preferable. Examples of colored metal oxides include: iron oxide, lower titanium oxide, copper oxide, cobalt oxide, chromium oxide and nickel oxide. Of these colored metal oxides, iron oxide is preferable.

Examples of colorless metals used for further coating the surface of the colored metal or colored metal oxide having already been applied a flaky powder in the present invention include: titanium, zirconium, zinc, tin, silicon and aluminum. Of these colorless metals, titanium is preferable. Examples of colorless metal oxides include: titanium oxide, zinc oxide and aluminum oxide. Of these colorless metal oxides, titanium oxide is preferable.

The pearl pigment of the present invention is such that the values a* and b* of the light reflected from the pigment powder (scattered light), which are measured in accordance with "the method for measuring the values a* and b* of the present invention", are 10 or less and preferably 5 or less.

As a measurement instrument applicable to such colorimetry, color measurement system GCMS series manufactured by Murakami Color Research Laboratory Co., Ltd. can be used.

The pearl pigment of the present invention is obtained by coating the surface of a flaky powder with a colored metal or colored metal oxide, as described above, and the average surface roughness of the colored metal or colored metal oxide is 10 nm or less and preferably 5 nm or less. Since colored metals or colored metal oxides have properties of absorbing light having particular wavelengths, the larger the roughness of the coating surface becomes, the more intense the scatter color becomes, resulting in the production of color of a low pearly luster. Decreasing the roughness of the coating surface retards the scattering of light, which makes it possible to obtain a pigment producing less scattered light, and hence more brilliant colors.

In the present invention, the term "average surface roughness (Ra)" indicates arithmetic average roughness, which is an average value of the measurements obtained by measuring the range of 2 μm×2 μm using an atomic force microscope (Nanoscope III by Digital Instrument) with a scan rate set to 1.0 Hz. When the measurement is made, the dispersion of the pearl pigment in a solvent such as ethanol is deposited on a flat base and then the solvent is removed to allow the pigment to closely attach to the base. The measurement is then made with an atomic force microscope.

In the pearl pigment of the present invention, the optical thickness of the colored metal or colored metal oxide coating layer is preferably 15 to 650 nm, more preferably 25 to 650 nm, and even more preferably 250 nm or less, and even more preferably 210 nm or less. If the optical thickness is larger than 650 nm, the absolute thickness of the absorption layer is increased and the effect of light absorption is also increased. Therefore, the pearl pigment preferably takes advantage of the color characteristic of the colored metal or colored metal oxide used. For example, in the case of iron oxide, when its optical thickness is larger than 250 nm, the pearl pigment is preferably a red pigment.

The optical thickness of the colored metal or colored metal oxide coating layer herein used means the thickness obtained by multiplying the geometric thickness of the coating layer by the refractive index of the same. In the case of iron oxide, the geometric thickness of the coating layer is preferably 80 nm or less and more preferably 50 nm or less, in the cases were scattered light is fully retarded, if iron oxide is used as the colored metal oxide, when the optical thickness of the coating layer is 120 to 210 nm, the interference light is gold, whereas when the optical thickness of the coating layer is 60 to 120 nm, the interference light is silver. The geometric thickness of the coating layer is determined with a SEM.

In the present invention, the pearl pigment is multi-layered by further coating the surface of the colored metal or colored metal oxide with a colorless metal or colorless metal oxide, and thus, pigments of various color tones, gold to green, which are not restricted by the color characteristic of iron oxide can be obtained. The optical thickness of the colorless metal or colorless metal oxide coating layer is preferably on average 180 to 900 nm. In case of titanium oxide, the geometric thickness of the coating layer is preferably 30 to 360 nm. If the scatter color is intense as in the case of conventional pearl pigments, the interference light is killed by the scatter color and is invisible to the naked eye. In the pearl pigment of the present invention, since the scatter color is retarded, interference light having colors other than those characteristic of the coated colored metal or colored metal oxide, such as gold or green, can also be produced. The pearl pigment thus obtained can produce interference colors of a high chroma, compared with the pearl pigment coated with a single layer.

Large optical thickness of iron oxide, etc., is advantageous when producing pigments having colors of a reddish shade, which are characteristic of iron oxide. If scatter color is retarded, brilliant red, compared with the colors of a reddish shade which is a color produced by conventional pigments, can be produced.

When the relationship $n_s < n > n_0$ holds, where $n_s$, n and $n_0$ are the refractive index of a flaky powder, that of a colored metal compound and that of a colorless metal compound, respectively, the index of reflection can be increased, and the chroma can be enhanced. Specifically, the combination of mica (refractive index 1.58), iron oxide ($Fe_2O_3$) (refractive index 3.01) and titanium oxide (refractive index 2.5 to 2.7) is preferable.

The pearl pigment of the present invention can be produced by selecting the rate of adding an aqueous solution of a colored metal oxide precursor, for example, using the neutralization titration method. The neutralization titration method is preferably used for decreasing the surface roughness of the colored metal or colored metal oxide.

(Production Process 1)

Specifically, the pearl pigment of the present invention can be produced by: adding an aqueous solution of a precursor of a colored metal oxide to an aqueous dispersion of a flaky powder so that the amount of metal ion is $5 \times 10^{-4}$ to $12 \times 10^{-4}$ mol/min per 100 g of the flaky powder; adding an alkaline solution to the mixed solution so that the pH of the mixed solution is 5 to 8; separating solid from the mixed solution; baking the solid at 500 to 1000° C. to obtain a pearl pigment; suspending the obtained pearl pigment in water; adding an aqueous solution of a precursor of a colorless metal or colorless metal oxide; adding an alkaline aqueous solution to the mixed solution so that the pH of the mixed solution is adjusted to 5 to 8; separating solid from the mixed solution; and baking the separated solid at 500 to 1000° C.

First, a flaky powder is dispersed in water and fully stirred to prepare an aqueous dispersion of the flaky powder. The slurry concentration of the dispersion is preferably 1 to 50% by weight for coating the surface of the flaky powder uniformly with a metallic compound.

Examples of precursors of a colored metal oxide include ferric nitrate, ferric chloride and ferric sulfate. The concentration of the aqueous solution of such a precursor is preferably 20 to 70% by weight.

The dispersion of the flaky powder is heated to 50 to 100° C. and preferably to 70 to 80° C., an acid is added to the dispersion to give an acidic dispersion, and an aqueous solution of a precursor of a colored metal oxide is added to the reaction mixed solution while keeping the pH of the reaction solution at 2 to 4 and preferably 2.5 to 3.5 by adding an alkaline aqueous solution. To realize a smooth coated state in which surface roughness is minimal, the aqueous solution of a precursor of a colored metal oxide is added at a rate that allows the amount of metal ion to be $5 \times 10^{-4}$ to $1.2 \times 10^{-4}$ mol/min per 100 g of the flaky powder an preferably $8 \times 10^{-4}$ to $11 \times 10^{-4}$ mol/min per 100 g of the flaky powder. If the rate of adding the aqueous solution of a precursor of a colored metal oxide is in such a range, the scattered light is retarded, and the resultant pigment can be a preferable one.

Examples of alkaline aqueous solutions used for pH adjustment include: aqueous solutions of sodium hydroxide, potassium hydroxide, sodium carbonate, potassium carbonate, sodium hydrocarbonate and potassium hydrocarbonate.

After completing the addition, the mixed solution is aged. Then, an alkaline aqueous solution is added to adjust the pH of the mixed solution to 5 to 8, and the solution is further aged. After separating the solid, the solid is rinsed to remove the salt and dried. The dried solid is then baked at 500 to 1000° C. and preferably at 700 to 800° C. for 30 to 180 minutes.

Then, an aqueous dispersion of the obtained colored metal oxide-coated flaky powder is prepared. The concentration of the slurry in the dispersion is preferably 1 to 50% by weight, from the viewpoint of uniformly coating the surface of the colored metal oxide-coated flaky powder with a colorless metal or colorless metal oxide.

Examples of precursors of a colorless metal oxide include: titanium sulfate and titanium tetrachloride. The concentration of their aqueous solutions is preferably 20 to 60% by weight.

The dispersion of the colored metal oxide-coated flaky powder is heated to 50 to 100° C. and preferably to 70 to 80° C., an acid is added to the dispersion to give an acidic dispersion, and an aqueous solution of a precursor of a colorless metal oxide is added to the reaction mixed solution while keeping the pH of the reaction solution at 1 to 5 and preferably 1 to 3 by adding an alkaline aqueous solution.

Examples of alkaline aqueous solutions used for pH adjustment are the same as described above.

After completing the addition, the mixed solution is aged. Then, an alkaline aqueous solution is added to adjust the pH of the mixed solution to 5 to 8, and the solution is further aged. After separating the solid, the solid is rinsed to remove the salt and dried. The dried solid is then baked at 500 to 1000° C. and preferably at 700 to 800° C. for 30 to 180 minutes. Thus, the pearl pigment of the present invention can be obtained.

(Production Process 2)

The pearl pigment of the present invention can also be produced by omitting the step of baking after coating a flaky powder with a precursor of a colored metal oxide and shifting to the step of coating the colored metal oxide-coated flaky powder with a colorless metal or colorless metal oxide. Specifically, the pearl pigment of the present invention can be obtained by: adding an aqueous solution of a precursor of a colored metal oxide to an aqueous dispersion of a flaky powder, just like the above described production process 1; adding an alkaline aqueous solution to adjust the pH of the mixed solution to 5 to 8; separating the solid from the mixed solution; rinsing the solid with water to remove the salt; and coating the surface of the solid thus obtained with a colorless metal or colorless metal oxide and baking the colorless-metal or colorless-metallic-oxide coated solid in the same manner as the production process 1.

The pearl pigment of the present invention can be used as a coloring material for, for example, cosmetics, coatings, printing inks, plastics, ceramics, or glaze for glasses.

The make-up cosmetics of the present invention contain the pigment described above. The surface of the pearl pigment can undergo hydrophobic treatment before use, from the viewpoint of improving the tenacity of the cosmetics. Hydrophobic treatment can be carried out by a conventional process using a hydrophobic treatment agent.

Examples of hydrophobic treatment agents which may be used include: silicone oil, fatty acid metal salt, alkyl phosphoric acid, alkali metal salts or amine salts of alkyl phosphoric acid, N-mono long chain (with 8 to 22 carbon atoms) aliphatic acyl-basic amino acid, and fluorine compound having perfluoroalkyl group.

Examples of silicone oils which may be used include: various types of chain silicone, cyclic silicone and modified silicone. Examples of metal salts of fatty acids used include: salts of fatty acids having 12 to 18 carbon atoms and calcium, magnesium, zinc, aluminum, or the like. Examples of alkyl phosphoric acids and the salts thereof used include: mono or di-esters containing alkyl or alkenyl group having 8 to 45 carbon atoms in total, or alkali metal salts or amine salts thereof. Examples of N-mono long chain aliphatic acyl-basic amino acids include: basic amino acids whose amino group at α- or ω-position is bound with acyl group having 8 to 22 carbon atoms, such as 2-ethyl hexanoyl, capryloyl, lauroyl, myristoyl, palmitoyl, stearoyl, isostearoyl, oleoyl, behenoyl, cocoyl, beef tallow fatty acid acyl or hydrogenated beef tallow fatty acid acyl. Examples of fluorine compounds containing perfluoroalkyl group include: those described in U.S. Pat. No. 3,632,744, JP-A-62-250074, JP-A-55-167209 and JP-A-2-218603.

In the hydrophobic treatment, the amount of hydrophobic treatment agent used is preferably 0.0005 to 0.2 parts by weight, and more preferably 0.02 to 0.1 parts by weight based on 1 part of pearl pigment, from the viewpoint of imparting sufficient hydrophobicity and a good feel for make-up cosmetics.

For the pearl pigments described above, more than one type can be used in combination. The amount of the pearl pigments contained in make-up cosmetics is preferably 0.1 to 30% by weight and more preferably 0.5 to 30% by weight, from the viewpoint of allowing the make-up cosmetics to fully produce the blend effect and of avoiding an unnatural look due to too much luster. The pearl pigment of the present invention can also be used in combination with conventionally used pearl pigments.

The make-up cosmetics of the present invention can be produced by a conventional process. They can be, for example, powdery face powder, cake-type face powder, face powder, powdery foundation, oil-based foundation, cream foundation, liquid foundation, concealer, lid rouge, lip cream, cheek rouge, eye shadow, eye liner or eyebrow pencil.

Preferably, the amount of the pearl pigment of the present invention contained in the make-up cosmetics, of the present invention is: 0.1 to 30% by weight and more preferably 0.5 to by weight, when the cosmetics are powdery face powder, cake-type face powder and face powder; 0.1 to 30% by weight and more preferably 0.5 to 30% by weight, when the cosmetics are powdery foundation and oil-based foundation; 0.1 to 30% by weight and more preferably 0.5 to 25% by weight, when the cosmetics are cream foundation, liquid foundation and concealer; 0.1 to 20% by weight and more preferably 0.5 to 1.5% by weight, when the cosmetics are lip rouge and lip cream; 0.1 to 30% by weight and more preferably 0.5 to 25% by weight, when the cosmetics are cheek rouge and eye shadow; and 0.1 to 30% by weight and more preferably 0.5 to 20% by weight, when the cosmetics are eye liner and eyebrow pencil.

The make-up cosmetics of the present invention may further include a lubricant whose viscosity is 1000 mPa·s or less at 25° C. From the viewpoint of feeling in use, the viscosity of the lubricant used is preferably in the range of 0.1 to 1000 mPa·s and more preferably in the range of 2 to 500 mPa·s.

Any lubricant, can be used as long as its viscosity is 1000 mPa·s or less. Examples of such lubricants include liquid paraffin, squalane, olive oil, ester oil, diglyceride, triglyceride, silicone oil, and fluorine lubricant having a perfluoroalkyl group. Of these lubricants, liquid paraffin, squalane, ester oil, silicone oil and fluorine lubricant having a perflueroalkyl group are preferably used.

More than one type of lubricant, can be used in combination. The amount of the lubricants used is preferably 0.5 to 60% by weight and more preferably 2 to 50% by weight per 100% of make-up cosmetics, from the viewpoint of being free from a sticky feeling when used.

To allow make-up cosmetics to have preferable spreadability and show expected optical characteristics when they are applied to the skin, the blending ration of the pearl pigment to lubricants is preferably 1/10 to 100/1.

The make-up cosmetics of the present invention may include, if necessary, ingredients blended in commonly used cosmetics, such as surfactant, water-soluble polymer, other powders, moisturizer, preservative, chemical, UV absorber, pigment, inorganic or organic salt, perfume, chelating agent, pH adjuster or water, besides the above described ingredients.

The following examples further describe and demonstrate embodiments of the present invention. The examples are given only solely for the purpose of illustration and are not to be construed as limitations of the present invention.

EXAMPLES

Example 1

80 g of flaky mica of 5 to 60 μm in particle size were added to and fully dispersed in 1.2 L of water, and the mica dispersion was heated to 80° C., an hydrochloric acid was added so that the pH of the dispersion was adjusted to 3. Then, 337 g of pre-prepared, ferric nitrate aqueous solution (17 parts by mass of ferric nitrate: 26 parts by mass of water) were added slowly, at a rate of $9\times10^{-4}$ mol iron ion concentration/min, to the mica dispersion while keeping the pH of the dispersion at 3 using sodium hydroxide aqueous solution. After completing the addition, the pH of the mixed solution was adjusted to 5 using sodium hydroxide aqueous solution. The pH-adjusted solution was filtered, and the obtained solid was rinsed to remove the salt, suction filtered, dried, and baked at 700° C. for 1 hour.

The resultant pearl pigment was such that a coating layer of very fine iron oxide particles 20 nm in geometric thickness was formed uniformly on the surface of the flaky mica. The surface roughness of the coating layer was measured to be 3.44 nm.

Then, 80 g of the above iron-oxide coated pearl pigment were added to and fully dispersed in 1.2 L of water, and the pigment dispersion was heated to 75° C., and hydrochloric acid was added so that the pH of the dispersion was adjusted to 1.6. Then, 240 g of 40% by weight titanium tetrachloride aqueous solution were added at a rate of 1.4 g/min to the dispersion while keeping the pH of the dispersion at 1.6 using 20% by weight sodium hydroxide aqueous solution. After that, the pH of the dispersion was adjusted to 7 using 20% by weight sodium hydroxide aqueous solution. Then, the dispersion was rinsed with water to remove the salt, suction filtered, dried, and baked at 700° C. for 90 minutes. Thus, a titanium oxide/iron oxide coated coloring pearl pigment having a gold interference color of a high chrome was obtained.

Example 2

An iron-oxide coated pearl pigment was produced in the same manner as Example 1, except that the amount of the ferric nitrate aqueous solution (17 parts by mass of ferric nitrate 26 parts by mass of water) added was changed from 337 g to 430 g. The obtained pigment was such that a coating layer of very fine iron oxide particles 30 nm in geometric thickness was formed uniformly on the surface of the flaky mica. The surface roughness of the coating layer was measured to be 4.30 nm.

Then, the same procedures as Example 1 were carried out, except that the amount of 40% by weight titanium tetrachloride aqueous solution added was changed from 240 g to 200 g, to obtain a titanium oxide/iron oxide-coated coloring pearl pigment having a gold interference color of a high chroma.

Example 3

An iron-oxide coated pearl pigment was produced in the same manner as Example 1, except that the amount of ferric nitrate aqueous solution (17 parts by mass of ferric nitrate 26 parts by mass of water) added was changed from 337 g to 544 g. The obtained pigment was such that a coating layer of very fine iron oxide particles 50 nm in geometric thickness was formed uniformly on the surface of the flaky mica. The surface roughness of the coating layer measured 3.03 nm.

Then, the same procedures as Example 1 were carried out provided that the amount of 40% by weight titanium tetrachloride aqueous solution added was changed from 240 g to 63 g, to obtain a titanium oxide/iron oxide-coated pearl pigment having a red interference color of a high chroma.

Example 4

An iron-oxide coated pearl pigment was produced in the same manner as Example 1, except that the amount of ferric nitrate aqueous solution (17 parts by mass of ferric nitrate 26 parts by mass of water) added was changed from 337 g to 544 g. The obtained pigment was such that a coating layer of very fine iron oxide particles 50 nm in geometric thickness was formed uniformly on the surface of the flaky mica. The surface roughness of the coating layer measured 3.03 nm.

Then, the same procedures as Example 1 were carried out, except that the amount of 40% by weight titanium tetrachloride aqueous solution added was changed from 240 g to 320 g, to obtain a titanium oxide/iron oxide-coated pearl pigment having a red interference color a high chroma.

Example 5

An iron oxide-coated pearl pigment was produced in the same manner as Example 1, except that the amount of ferric nitrate aqueous solution (17 parts by mass of ferric nitrate 26 parts by mass of water) added was changed from 337 g to 430 g. The obtained pigment was such that a coating layer of very fine iron oxide particles 30 nm in geometric thickness was formed uniformly on the surface of the flaky mica. The surface roughness of the coating layer was measured to be 4.30 nm.

Then, the same procedures as Example 1 were carried out, except that the amount of 40% by weight titanium tetrachloride aqueous solution added was changed from 240 g to 350 g, to obtain a titanium oxide/iron oxide-coated pearl pigment having a green interference color of a high chroma.

Example 6

80 g of flaky mica of 5 to 60 µm in particle size were added to and fully dispersed in 1.2 L of water, and toe mica dispersion was heated to 80° C., and hydrochloric acid was added so that the pH of the dispersion was adjusted to 3. Then, 337 g of pre-prepared ferric nitrate aqueous solution (17 parts by mass of ferric nitrate: 26 parts by mass of water) were added slowly, at a rate of $9\times10^{-4}$ mol iron ion concentration/min, to the mica dispersion while keeping the pH of the dispersion at 3 using sodium hydroxide aqueous solution. After completing the addition, the pH of the mixed solution was adjusted to 5 using sodium hydroxide aqueous solution. The obtained slurry-like reaction product was filtered and rinsed to remove the salt. Then, the moisture content of the slurry-like reaction product was measured and the slurry-like reaction product was weighed so that its solid content was 80 g. Subsequently, water was added to give a 1.2 L of reaction product solution, and the reaction product was fully dispersed in the water, and the dispersion was heated to 75° C. After completing the heating, hydrochloric acid was added so that the pH of the dispersion was 1.6. Then, the same procedure as Example 1 was carried out, and titanium tetrachloride aqueous solution was added to the dispersion and baked at 700° C. for 90 minutes. Thus, a titanium oxide/iron oxide-coated coloring pearl pigment having a gold interference color of a high chroma was obtained.

Example 7

An iron oxide-coated pearl pigment was produced in the same manner as Example 1, except that the amount of ferric nitrate aqueous solution (17 parts by mass of ferric nitrate 26 parts by mass of water) added was changed from 337 g to 140 g. The obtained pigment was such that a coating layer of very fine iron oxide particles of 10 nm in geometric thickness (30 nm in optical thickness) was formed uniformly on the surface of the flaky mica. The surface roughness of the coating layer was measured to be 8.3 nm.

Then, the same procedures as Example 1 were carried out, except that the amount of 40% by weight titanium tetrachloride aqueous solution added was changed from 240 g to 260 g, to obtain a titanium oxide/iron oxide-coated pearl pigment having a gold interference color of a high chroma.

Example 8

An iron-oxide coated pearl pigment was produced in the same manner as Example 1, provided that the amount of ferric nitrate aqueous solution (17 parts by mass of ferric nitrate 26 parts by mass of water) added was changed from 337 g to 140 g. The obtained pigment was such that a coating layer of very fine iron oxide particles of 10 nm in geometric thickness was formed uniformly on the surface of the flaky mica. The surface roughness of the coating layer measured 8.5 nm.

Then, the same procedures as Example 1 were carried out, except that the amount of 40% by weight titanium tetrachloride aqueous solution added was changed from 240 g to 150 g, to obtain a titian oxide/iron oxide-coated pearl pigment having a red interference color of a high chroma.

Example 9

An iron-oxide coated pearl pigment was produced in the same manner as Example 1, provided that the amount of ferric nitrate aqueous solution (17 parts by mass of ferric nitrate 26 parts by mass of water) added was changed from 337 g to 65 g. The obtained pigment was such that a coating layer of very fine iron oxide particles of 5 nm in geometric thickness (15 nm in optical thickness) was formed uniformly on the surface of the flaky mica. The surface roughness of the coating layer was measured to be 3.5 nm.

Then, the same procedures as Example 1 were carried out, except that the amount of 40% by weight titanium tetrachloride aqueous solution added was changed from 240 g to 305 g, to obtain a titanium oxide/iron oxide-coated pearl pigment having a gold interference color of a high chrome.

Example 10

An iron-oxide coated pearl pigment was produced in the same manner as Example 1, provided that the amount of ferric nitrate aqueous solution (17 parts by mass of ferric nitrate: 26 parts by mass of water) added was changed from 337 g to 65 g. The obtained pigment was such that a coating layer of very fine iron oxide particles 5 nm in geometric thickness (15 nm in optical thickness) was formed uniformly on the surface of the flaky mica. The surface roughness of the coating layer measured 3.5 nm.

Then, the same procedures as Example 1 were carried out, provided that the amount of 40% by weight titanium tetrachloride aqueous solution added was changed from 240 g to 170 g, to obtain a titanium oxide/iron oxide-coated pearl pigment having a red interference color of a high chrome.

Example 11

An iron-oxide coated pearl pigment was produced in the same manner as Example 1, except that the amount of ferric nitrate aqueous solution (17 parts by mass of ferric nitrate 26 parts by mass of water) added was changed from 337 g to 65 g. The obtained pigment was such that a coating layer of very fine iron oxide particles 5 nm in geometric thickness was formed uniformly on the surface of the flaky mica. The surface roughness of the coating layer was measured to be 3.5 nm.

Then, the same procedures as Example 1 were carried out, except that the amount of 40% by weight titanium tetrachloride aqueous solution added was changed from 240 g to 251 g, to obtain a titanium oxide/iron oxide-coated pearl pigment having a green interference color of a high chrome.

Comparative Example 1

120 g of flaky mica of 5 to 60 µm in particle size were added to 820 g of water and heated to 95° C. A solution of 350 g of urea, 170 g of ferrous sulfate, 10 g of ferric nitrate and 7 g of 30% nitric acid aqueous solution in 308 g of water was added dropwise to the above mica dispersion at a rate of about 25 g/min over 35 minutes. Then the mixed solution was stirred for 2 hours, and 205 g of 30% potassium carbonate aqueous solution were added dropwise to the mixed solution over about 40 minutes. Then, the solution was rinsed with water to remove the salt, suction filtered, dried, and baked at 700° C. for 1 hour. The obtained pigment was such that a coating layer of about 0.1-µm iron oxide particles 30 nm in geometric thickness was formed a little roughly on the surface of the flaky mica. The surface roughness of the coating layer was measured to be 13.41 nm.

Then, the same procedures as Example 1 were carried out, provided that the amount of 10% by weight titanium tetrachloride aqueous solution added was changed from 240 g to 200 g, to obtain a titanium oxide/iron oxide-coated pearl pigment having a gold interference color.

Test Examples

The values a* and b* of light reflected from powder and the geometric thickness of coating layer were determined for the pearl pigments obtained in Examples 1 to 5 and Comparative Example 1 and commercially available, titanium-oxide coated mica (Flamenco Gold, Flamenco Red manufactured by ENGELHARD) (1) The values a* and b* of light reflected from powder were measured in accordance with "the method for measuring the values a* and b* of the present invention". As a spectrophotometric colorimeter, used was GCMS-4, manufactured by Murakami Color Research Laboratory Co Ltd., provided with sheet polarizer (Polaroid, Type HN32). As a light source, a halogen lamp (HLWS7) by NARVA Speziallampen GmbH was used. Measurement samples were prepared by using pieces of black artificial leather (Okamoto, Type: OR-7) and coating the area 5 cm×10 cm of each piece uniformly with each pigment powder using a sponge so that the amount of the coating applied was on average 0.05 mg/cm².

The geometric thickness of each coating layer was measured with SEM. The geometric thickness was obtained by first measuring the thickness of the flaky powder before coating and then measuring the thickness of the pearl pigment after coating. The optical thickness was obtained by multiplying the geometric thickness of the coating layer by the refractive index of the same. The refractive index of iron oxide ($Fe_2O_3$) used was 3.0 and that of titanium oxide was 2.5. The results are shown in Table 1.

(2) The values a* and b* of light reflected from powder were also measured under the above described conditions in accordance with the commonly used colorimetry (measurement angle of 45°) in which no sheet polarizer was used. The values c* and h indicate the chroma and hue angle standardized by Commission International de L'Eclairage (CIE) (1976). The results are shown in Table 2.

The results shown in Table 2 prove that in the pearl pigments of the present invention, the values c* are larger than those of the comparative example and commercially available pigments that have the same hue angle, in other words, the pearl pigments of the present invention are brighter. This indicates that in the pearl pigments of the present invention, interference colors are obtained free from the restriction from the color of the color metallic compounds themselves.

TABLE 1

|  | Appearance of Sample | Geometric Thickness of Iron Oxide Coating [Optical Thickness] (nm) | Geometric Thickness of Titanium Oxide Coating [Optical Thickness] (nm) | Value a* | Value b* |
|---|---|---|---|---|---|
| Example 1 | Gold pearl | 20 [60] | 140 [350] | 7.6 | 4.5 |
| Example 2 | Gold pearl | 30 [90] | 130 [325] | 6.3 | 1.3 |
| Example 3 | Red pearl | 50 [150] | 80 [200] | 5.5 | 0.2 |
| Example 4 | Red pearl | 50 [150] | 140 [350] | 5.0 | 4.1 |
| Example 5 | Green pearl | 30 [90] | 220 [550] | 8.8 | 7.4 |
| Example 6 | Gold pearl | 20 [60] | 140 [350] | 3.8 | 2.4 |
| Example 7 | Gold pearl | 10 [30] | 160 [400] | 3.5 | 3.0 |
| Example 8 | Red pearl | 10 [30] | 130 [320] | 3.4 | 2.8 |
| Example 9 | Gold pearl | 5 [15] | 170 [425] | 4.5 | 3.0 |
| Example 10 | Red pearl | 5 [15] | 130 [325] | 5.0 | 4.2 |
| Example 11 | Green pearl | 5 [15] | 160 [400] | 6.3 | 7.2 |
| Comparative Example 1 | Gold pearl | 30 [90] | 130 [325] | 10.8 | 9.3 |

*Commercially available pigments are excluded because they contain no colored metals in their inner layers.

TABLE 2

|  | Appearance of Sample | Geometric Thickness of Iron Oxide Coating [Optical Thickness] (nm) | Geometric Thickness of Titanium Oxide Coating [Optical Thickness] (nm) | Value a* | Value b* | Value c* | Value h |
|---|---|---|---|---|---|---|---|
| Example 1 | Gold pearl | 20 [60] | 140 [350] | −6.5 | 47.3 | 48 | 98 |
| Example 2 | Gold pearl | 30 [90] | 130 [325] | −5.3 | 48.3 | 49 | 96 |
| Example 3 | Red pearl | 50 [150] | 80 [200] | 35.3 | −4.1 | 36 | 353 |
| Example 4 | Red pearl | 50 [150] | 140 [350] | 25.2 | −11.5 | 28 | 335 |
| Example 5 | Green pearl | 30 [90] | 220 [550] | −7.9 | 4.7 | 9 | 149 |
| Example 6 | Gold pearl | 20 [60] | 140 [350] | −11.7 | 43.5 | 45.1 | 105 |
| Example 7 | Gold pearl | 10 [30] | 160 [400] | −6.8 | 49.6 | 50 | 98 |
| Example 8 | Red pearl | 10 [30] | 130 [320] | 33.5 | −3.9 | 34 | 353 |
| Example 9 | Gold pearl | 5 [15] | 170 [425] | −5.6 | 50.7 | 51 | 96 |
| Example 10 | Red pearl | 5 [15] | 130 [325] | 30.2 | −13.8 | 33 | 335 |
| Example 11 | Green pearl | 5 [15] | 160 [400] | −15.8 | 9.4 | 18 | 148 |
| Comparative Example 1 | Gold pearl | 30 [90] | 130 [325] | −5.9 | 25.7 | 26 | 103 |
| Commercially available pigment 1 | Gold pearl | Flamenco Gold | | −6.5 | 30.1 | 31 | 102 |
| Commercially available pigment 2 | Red pearl | Flamenco Red | | 17.1 | −0.6 | 17 | 358 |

Applications

Applications of coatings, inks and plastics in which pearl pigments obtained in examples are used will be shown below.

Application 1 (Coating for Automobiles)

A steel sheet with an intermediate coating applied to an electrodeposition coating was prepared. A color base coating was applied onto the surface of the intermediate coating, and the resultant steel sheet was baked at 140° C. for 30 minutes to be dried. Then, a base coating was prepared which was a resin fluid made up of acrylic resin and melamine resin and containing 5% by weight of pearl pigment obtained in Example 1 and spray coated on the surface of the above color base coating so that the coating thickness was 15 μm. Subsequently, an acryl-melamine clear coating was applied to the surface of the base coating by wet-on-wet spray coating so that the coating thickness was 40 μm, and the resultant steel sheet was baked at 140° C. for 30 minutes so that the base coating and the clear coating was integrally cured. The coated steel sheet thus obtained had a lustrous interference color of brilliant gold.

Application 2 (Printing Ink Composition)

The ingredients shown in Table 3 were mixed, and the mixture was kneaded with a sand m±1.1 to obtain a printing ink composition.

Printing was performed on black paper using the obtained printing ink composition so that the thickness of the coating (after drying) was 50 μm. The coating had a lustrous interference color of brilliant gold.

TABLE 3

| Ingredients | Content (parts by weight) |
|---|---|
| Pearl pigment of Example 1 | 12.5 |
| Acrylic resin | 25.0 |
| Naphtha | 30.0 |
| Butylcellosolve | 32.5 |

Application 3 (Plastic-Coloring Composition)

The ingredients shown in Table 4 were mixed with a Henschel mixer, and the obtained mixture was formed into colored pellets with an extruding machine. Then the pellets were formed into platelet-shaped pieces 90×50×2 mm in size in an extruder. The formed pieces had a lustrous interference color of brilliant, red.

TABLE 4

| Ingredients | Content (parts by weight) |
|---|---|
| Pearl pigment of Example 3 | 2.0 |
| Polyethylene resin | 97.5 |
| Dibutylhydroxytoluene (antioxidant) | 0.5 |

Examples 12 to 15, Comparative Examples 1 to 2

Cake-type foundations each having the compositions shown in Table 5 were produced. The produced cake-type foundations were evaluated in terms of creating: a smooth finish, a light skin color, the smallest possible color difference between the forehead portion and the side cheek portion, and a natural luster. The evaluations are also shown in Table 5, (Production Process)

The ingredients (1) to (13) were mixed while stirring, and then the ingredients (14) to (16) were added and mixed. Each mixture was pulverized with an atomizer and sieved, and the sieved powder was packed in a metal dish and compressed to obtain a cake-type foundation.

(Evaluation Method)

Twenty panels for cosmetics were allowed to use each of the produced cake-type foundations and scored points based on the criteria shown below. The quality of the foundations was judged using the average value of the points scored by the panels.

(1) creates an attractive skin look, creates a smooth finish, creates a light skin color, creates natural luster;

5 points very good
    4 points: good
    3 points: fair
    2 points: a little poor
    1 point: poor (2) color difference between the forehead portion and the side cheek portion 5 points: almost no difference
    4 points small difference
    3 points: somewhat difference
    2 points: a little large difference
    1 point: large difference

TABLE 5

| Ingredients | Examples | | | | Comparative Examples | |
|---|---|---|---|---|---|---|
| (% by weight) | 12 | 13 | 14 | 15 | 1 | 2 |
| (1) Pearl pigment (Example 1) | 10 | | | | | |
| (2) Pearl pigment (Example 2) | | 10 | | | | |
| (3) Pearl pigment (Example 9) | | | 10 | | | |
| (4) Pearl pigment (Example 10) | | | | 10 | | |
| (5) Talc | 20 | 20 | 20 | 20 | 20 | 20 |
| (6) Sericite | 31.5 | 31.5 | 31.5 | 31.5 | 41.5 | 31.5 |
| (7) Spherical nylon | 5 | 5 | 5 | 5 | 5 | 5 |
| (8) Zinc stearate | 3 | 3 | 3 | 3 | 3 | 3 |
| (9) Mica titanium* | | | | | | 10 |
| (10) Titanium dioxide | 10 | 10 | 10 | 10 | 10 | 10 |
| (11) Yellow iron oxide | 7 | 7 | 7 | 7 | 7 | 7 |
| (12) Red iron oxide | 2 | 2 | 2 | 2 | 2 | 2 |
| (13) Black iron oxide | 1 | 1 | 1 | 1 | 1 | 1 |
| (14) Paraben | 0.5 | 0.5 | 0.5 | 0.5 | 0.5 | 0.5 |
| (15) Dimethyl polysiloxane (10 mPa·s) | 5 | 5 | 5 | 5 | 5 | 5 |
| (16) Liquid paraffin (10 mPa·s) | 5 | 5 | 5 | 5 | 5 | 5 |
| Creates a smooth finish | 4.7 | 4.7 | 4.7 | 4.3 | 1.3 | 4.5 |
| Creates a light skin color | 4.5 | 4.3 | 4.8 | 4.3 | 1.9 | 4.7 |
| Creates the smallest color difference between the forehead portion and the side cheek portion | 4.6 | 4.7 | 4.5 | 4.7 | 4.8 | 2.2 |
| Creates a natural luster | 4.7 | 4.7 | 4.7 | 4.2 | 3.0 | 2.2 |
| Creates an attractive skin look | 4.7 | 4.7 | 4.7 | 4.5 | 2.2 | 3.0 |

*Flamenco Gold manufactured by ENGELHARD

What is claimed is:

1. A process for producing a pearl pigment comprising:
(A) adding an aqueous solution of a colored metal oxide precursor to an aqueous dispersion of a flaky powder so that the amount of metal ion is $5 \times 10^{-4}$ to $12 \times 10^{-4}$ mol/min per 100 g of the flaky powder;
adding an alkaline solution to the mixed solution so that the pH of the mixed solution is adjusted to 5 to 8;
separating the solid from the mixed solution; baking the separated solid at 500 to 1000° C. to obtain a pearl pigment;
suspending the obtained pearl pigment in water;
adding an aqueous solution of a colorless metal or colorless metal oxide precursor to the suspension;
adding an alkaline solution to the mixed solution so that the pH of the mixed solution is adjusted to 5 to 8;
separating the solid from the mixed solution; and
baking the separated solid at 500 to 1000° C.; or
(B) adding an aqueous solution of a colored metal oxide precursor to an aqueous dispersion of a flaky powder so that the amount of metal ion is $5 \times 10^{-4}$ to $12 \times 10^{-4}$ mol/min per 100 g of the flaky powder;
adding an alkaline solution to the mixed solution so that the pH of the mixed solution is adjusted to 5 to 8;
separating the obtained solid from the mixed solution;
adding an aqueous solution of a colorless metal or colorless metal oxide precursor to a dispersion of the solid;
separating the obtained solid from the mixed solution; and
baking the separated solid at 500 to 1000° C.

2. The process of for producing a pearl pigment according to claim 1 that comprises (A).

3. The process of for producing a pearl pigment according to claim 1 that comprises (B).

4. The process for producing a pearl pigment according to claim 1, wherein when the aqueous solution of the colored metal oxide precursor is added to the aqueous dispersion of the flaky powder, the temperature of the mixed solution is in the range of 50 to 100° C.

5. The process for producing a pearl pigment according to claim 1, wherein when the aqueous solution of the colored metal oxide precursor is added to the aqueous dispersion of the flaky powder, the pH of the mixed solution is in the range of 2 to 4.

6. The process for producing a pearl pigment according to claim 1, wherein the colored metal oxide precursor is an iron oxide precursor.

* * * * *